(12) United States Patent
Weston et al.

(10) Patent No.: US 6,719,980 B1
(45) Date of Patent: Apr. 13, 2004

(54) STRUCTURAL PROTEINS OF FISH PANCREATIC DISEASE VIRUS AND USES THEREOF

(75) Inventors: Jonathan Weston, Belfast (GB); Daniel Todd, Belfast (GB)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/674,866

(22) PCT Filed: May 6, 1999

(86) PCT No.: PCT/EP99/03244
§ 371 (c)(1),
(2), (4) Date: Jun. 4, 2001

(87) PCT Pub. No.: WO99/58639
PCT Pub. Date: Nov. 18, 1999

(30) Foreign Application Priority Data

May 8, 1998 (EP) .............................................. 98201461

(51) Int. Cl.⁷ ..................... A61K 39/12; A61K 39/193; C12Q 1/70; G01N 33/53; C07K 17/00
(52) U.S. Cl. ................ 424/218.1; 424/204.1; 435/5; 435/7.1; 530/350
(58) Field of Search ........................... 424/204.1, 218.1; 435/5, 7.1; 530/350

(56) References Cited

U.S. PATENT DOCUMENTS 5,939,073 A * 8/1999 McLoughlin et al. .... 424/218.1

FOREIGN PATENT DOCUMENTS

| EP | 0 712 926 | 5/1996 |
| EP | 0 712 926 A2 * | 5/1996 |

OTHER PUBLICATIONS

Schlesinger et al. Togaviridae: The Viruses and Their Replication. In B.N. Fields et al. (ed.), Fields Virology, 3rd ed. Philadelphia: Lippencott–Raven Publishers; 1996: 825–827.*

Houghton, G., "Acquired Protection in Atlantic Salmon Salmo Salar Parr and Post–Smolts Against Pancreas Disease" vol. 18 No. 2, Feb. 24, 1994. p. 109–118.

Nelson, R., et al. "Isolation of a Toga–Like Virus from Farmed Atlantic Salmon Salmo Salar with Pancreas Disease" Diseases of Aquatic Organism. vol. 22, No. 1, May 4, 1995, p. 25–32.

* cited by examiner

Primary Examiner—James Housel
Assistant Examiner—Shanon Foley
(74) Attorney, Agent, or Firm—Mark W Milstead

(57) ABSTRACT

The present invention relates to the structural proteins of the causative agent of Pancreatic Disease in fish, nucleotide sequences encoding said proteins, vaccines comprising said proteins or nucleotide sequences and diagnostic kits comprising said proteins or nucleotide sequences.

4 Claims, 2 Drawing Sheets pFastBac1 SPDV Constructs

1. p130  *Not*1 —[ Capsid | E3 | E2 | 6K | E1 | 3'NCR ]— *Not*1
3944nt

2. p98  *Not*1 ATG —[ E3 | E2 | 6K | E1 | 3'NCR ]— *Not*1
3098nt

3. PE2 (E3&E2)  *Not*1 ATG —[ E3 | E2 ]— UGA *Not*1
1527nt

4. E2  *Not*1 ATG —[ E2 ]— UGA *Not*1
1314nt

FIGURE 1

```
TGC AGC AGG GTG CGG TAC TCT CTG GTC GCC AAC
 C   S   R   V   R   Y   S   L   V   A   N

ACG TTC AAC CCG AAC CCA CCA CCA TTG ACC GCA
 T   F   N   P   N   P   P   P   L   T   A
                                        E2 C-TERMINUS
CTG ACT GCA GCA CTG TGT TGC ATA CCA GGG GCT
 L   T   A   A   L   C   C   I   P   G   A
        | 6K PROTEIN
CGC GCG GAC CAA CCC TAC TTG GAC ATC ATT GCC   (27)
 R   A   D   Q   P   Y   L   D   I   I   A    (9)

TAC TTG TGG ACC AAC AGC AAA GTG GCC TTC GGG   (60)
 Y   L   W   T   N   S   K   V   A   F   G    (20)

CTA CAA TTT GCG GCG CCC GTG GCC TGT GTG CTC   (93)
 L   Q   F   A   A   P   V   A   C   V   L    (31)

ATC ATT ACA TAC GCC CTT AGG CAC TGC AGA TTG   (126)
 I   I   T   Y   A   L   R   H   C   R   L    (42)

TGC TGC AAG TCT TTT TTA GGG GTA AGA GGG TGG   (159)
 C   C   K   S   F   L   G   V   R   G   W    (53)

TCA GCC CTG CTG GTC ATC CTT GCG TAT GTA CAG   (192)
 S   A   L   L   V   I   L   A   Y   V   Q    (64)
              | E1 N-TERMINUS
AGC TGC AAG AGC TAC GAA CAC ACC GTG GTG GTC   (204)
 S   C   K   S   Y   E   H   T   V   V   V    (68)

CCA ATG GAT CCA AGA GCC CCG TCG TAC GAA GCA
 P   M   D   P   R   A   P   S   Y   E   A

GTG ATA AAC CGG AAT GGG TAT GAT CCA TTG AAG
 V   I   N   R   N   G   Y   D   P   L   K

CTG ACC ATC TCA GTG AAT TTC ACC GTC ATC TCA
 L   T   I   S   V   N   F   T   V   I   S

CCA ACT ACG GCT CTG GAA T    3'
 P   T   T   A   L   E
```

FIGURE 2

STRUCTURAL PROTEINS OF FISH PANCREATIC DISEASE VIRUS AND USES THEREOF

FIELD OF THE INVENTION

The present invention relates to the structural proteins of the causative agent of Pancreatic Disease in fish, nucleotide sequences encoding said proteins, vaccines comprising said proteins or nucleotide sequences and diagnostic kits comprising said proteins or nucleotide sequences.

BACKGROUND OF THE INVENTION

Pancreatic Disease (PD) is a serious disease that affects fish, in particular salmonid fish such as wild Atlantic salmon, rainbow trout and the like. The disease causes lesions in the pancreas, including loss of pancreatic exocrine tissue, and fibrosis, cardiac and skeletal muscle myopathies. Outbreaks of PD were first described in 1984 by Munro et al, in Helgoland Meeresuntersuchungen 37:571–586 (1984). PD typically affects the fish post-molts during the first year after they are transferred to sea sites and is reported to spread rapidly among farm fish held in sea cages. Clinical signs include lethargy with a tendency to congregate in cage corners and to fail to maintain a horizontal position, cessation of feeding (anorexia) and significant mortalities (Ferguson et al, J. Fish Disease 9:95–98, 1986). Murphy et al (in J. Fish Disease 15:401–408, 1992) confirmed these observations in a later study, in which it was found that cardiac and skeletal myopathy is exacerbated in fish suffering from PD.

An outbreak of PD in a fish farm can cause growth to be reduced and up to 10 percent of surviving fish may prove to be runt. On Irish fish farms PD causes significant mortality rates of 10 to 60 percent among the young fish during the first year after they are transferred to sea sites (McLoughlin, M., Fish Farmer page 19, March/April 1995). The estimated cost to the Irish industry in terms of loss of production is currently thought to be around £25 million per year. Consequently, there is a great need for a vaccine for the prevention and/or treatment of PD in fish.

EP-A-712926 describes the isolation of the causative agent of PD from tissues of PD affected fish and the identification of the virus as a toga-like virus. To prevent PD infections in fish, the use of attenuated or inactivated PD for vaccination of the fish is accordingly suggested. A drawback in the production of inactivated vaccines from the PD virus described in EP-A-712926 is the slow growth of the virus, in particular on cell cultures, which makes the manufacturing of said vaccines a relatively inefficient process. A further drawback with the inactivated vaccines is the instability of the inactivated virus in the presence of other inactivated pathogens resulting in potency loss. Fish vaccines are generally produced as multivalent vaccines, and significant higher amounts of inactivated virus are required in the multivalent vaccine than would be necessary in a monovalent vaccine to compensate for the loss of potency.

SUMMARY OF THE INVENTION

The present invention provides the means to produce alternative vaccines to prevent infection of fish with PD, in which the above mentioned difficulties are overcome.

BRIEF DESCRIPTION OF THE FIGURES

FIG. 1 shows the structural organisation of the various cloned nucleotide sequences coding for the PD structural proteins.

FIG. 2 shows the nucleotide sequence of C-terminus of E2 gene/"long" 6K gene/N-terminus of E1 gene. The putative cleavage sites between the E2/6K protein and 6K/E1 protein are represented by the vertical line (|)The nucleotide sequence encoding the "long" 6K protein is 204 nucleotides long and encodes a protein of 68 amino acids. The numbering between brackets on the right of the sequence refers to the nucleotide and amino acid residues of the 6K gene or protein, respectively. At nucleotide position 44 of the nucleotide sequence encoding the 6K gene, the G-residue can be replaced with an A residue, resulting in a 6K protein with an N residue at amino acid position 15 of the amino acid sequence depicted in the figure.

DETAILED DESCRIPTION OF THE INVENTION

The present invention provides for the nucleotide sequence of the 3' part of the genomic RNA of a salmon PD virus (SPDV). This sequence of 5179 nucleotides is depicted in SEQ ID NO 1 and contains several open reading frames (ORF's): On the coding strand nucleotide 2 to 1186 codes for a non-structural protein, and another overlapping ORF starting from nucleotide 997 to 5076 codes for the structural proteins. This ORF was designated as p130. Other non-determined ORF's were found on the coding strand (3447 to 3767 and 4289 to 4612) and the non coding strand (1207 to 890, and 1232–837).

The ORF from nucleotide 2 to 1186 codes for the C-terminal part of a non-structural protein designated as NSP4; its deduced amino acid is depicted in SEQ ID NO 2.

ORF p130 comprises the nucleotide sequences that encode the structural proteins of the PD virus. The structural proteins of the PD virus consist of a basic capsid protein, three envelope proteins designated as E1, E2 and E3, and a protein designated as the 6K protein. The amino acid sequence of the whole protein encoded by the p130 ORF is depicted in SEQ ID NO 3. After processing, the p130 protein is spliced into the capsid protein (aa 76–375 of p130), E3 (aa 358–428 of p130), E2 (aa429–866 of p130), 6K (aa 867–898 of p130), and E1 (aa 899–1359 of p130).

The nucleotide sequence encoding the capsid protein of the PD virus is located at nucleotide 1222 to 2067 of SEQ ID NO 1. The corresponding amino acid sequence (total 282 amino acids) is depicted in SEQ ID NO 4.

The nucleotide sequence encoding the envelope proteins E3, E2 and E1 are located at nucleotides 2068–2280, 2281–3594 and 3691–5076 respectively, of the nucleotide sequence depicted in SEQ ID NO 1. The corresponding amino acid sequences of the E3, E2 and E1 proteins are depicted in SEQ ID No's 5, 6 and 8 respectively.

The nucleotide sequence encoding the 6K protein is located at nucleotide 3595 to 3690 of the nucleotide sequence depicted in SEQ ID NO 1, and the corresponding amino acid sequence of the 6K protein is depicted in SEQ ID NO 7. Further sequence analysis of the viral RNA extracted from PD infected pancreas tissue revealed the existence of a longer variant of the 6K protein having 68 amino acids in length compared to the 6K protein of 32 amino acids depicted in SEQ ID NO 7. The nucleotide sequence (SEQ ID NO 14) encoding the longer variant of 6K protein is 204 nucleotides in length compared to the 96 nucleotides of the nucleotide sequence encoding the truncated 6K protein. The nucleotide sequence encoding the long variant of 6K protein and the deduced amino acid sequence thereof are shown in FIG. 2 and SEQ ID NO 14 and SEQ ID NO 15 respectively.

The cloning and characterisation of the nucleotide sequences of the present invention provides for the production of the structural proteins of the PD virus using standard recombinant DNA technology (Sambrooke et al., Molecular Cloning: a Laboratory Manual, Cold Spring Harbor Laboratory Press, Cold Spring Harbor, 1989). Cloning techniques and subsequent protein expression using in vitro expression systems are well known in the art. In this way, recombinant structural PDV proteins can be obtained, that are substantially free from other PDV proteins. These isolated structural proteins can be used to manufacture subunit vaccines to protect against infection of PD in fish. The subunit vaccines may be used as marker vaccines in fish to distinguish vaccination from field infections with PD. Alternatively the nucleotide sequences encoding the structural proteins of the PD virus can be used to manufacture DNA vaccines or vector vaccines to protect against infection of fish with PD. The nucleotide sequences and recombinant PD proteins can furthermore be used for diagnostic purposes, for instances to detect the presence of PD virus in the field or anti-PD antibodies in fish. Additionally, the recombinant PD proteins of the present invention can be used to produce PD specific antibodies. These antibodies can also be used for diagnostic purposes such as the detection of PD virus in fish or in the field.

Thus, in a first aspect the invention provides for a nucleic acid comprising the nucleotide sequence depicted in SEQ ID NO 1 encoding the structural proteins and part of NSP4 of the PD virus, fragments of said nucleotide sequence and a nucleic acid comprising the nucleotide sequence depicted in SEQ ID NO 14. Preferred fragments of the nucleotide sequences according to the invention are nucleotide fragments 1222–5076 (also referred to as p130 encoding the capsid, E3, E2, 6K and E1 proteins), 2068–5076 (also referred to as p98 encoding the E3, E2, 6K and E1 proteins), 2068–3594 (also referred to as pE2 encoding E3 and E2 proteins), 1222–2067 (capsid), 2068–2280 (E3), 2281–3594 (E2), 3595–3690 (6K), and 3691–5076 (E1). For the purpose of this invention the nucleotide sequences according to the present invention also encompass the nucleotide sequence depicted in SEQ ID NO 1 and fragment sequences thereof (such as the p130 and p98 fragments) which at least comprise a nucleotide sequence encoding for a 6K protein, wherein the nucleotide sequence depicted by nucleotide 3595–3690 of SEQ ID NO 1 has been substituted with the nucleotide sequence depicted in SEQ ID NO 14.

Also within the scope of this invention are nucleotide sequences comprising tandem arrays of the nucleic acid comprising the sequence depicted in SEQ ID NO 1 or SEQ ID NO 14 or fragments thereof. Nucleotide sequences that are complementary to the sequence depicted in SEQ ID NO 1, SEQ ID NO 14, or parts thereof are also within the scope of the invention, as well as nucleotide sequences that hybridise with the sequence depicted in SEQ ID NO 1 or SEQ ID NO 14. The hybridisation conditions for this purpose are stringent, preferably highly stringent. According to the present invention the term "stringent" means washing conditions of 1×SSC, 0.1% SDS at a temperature of 65° C.; highly stringent conditions refer to a reduction in SSC towards 0.3×SSC.

Nucleotide sequences that hybridise with the sequence shown in SEQ ID NO 1 or SEQ ID NO 14 are understood to be nucleotide sequences that have a sequence homology of at least 70%, preferably 80%, more preferably 90% with the corresponding matching part of the sequence depicted in SEQ ID NO 1 or SEQ ID NO 14. According to the present invention the sequence homology is determined by comparing the nucleotide sequence with the corresponding part of the sequence depicted in SEQ ID NO 1 or SEQ ID NO 14.

The sequence homology between a nucleotide and the sequence in SEQ ID NO 1 or SEQ ID NO 14 can be determined via common sequence analysis program such as BLASTN and the like. The optimal match area is automatically determined by these programs. Homologous sequences can easily be isolated from closely related PD virus strains with the sequence depicted in SEQ ID NO 1 or SEQ ID NO 14 or fragments of these sequences using routine cloning and hybridisation techniques. Sleeping Disease (SD) virus is closely related to PD virus and the nucleic acid sequences encoding the structural capsid, E3, E2, E1 and 6K proteins of SD virus have the necssary sequence homology with the nucleic acid sequences depicted in SEQ ID NO 1 and 14. Thus these SD nucleic acid sequences are also within the present invention.

The nucleotide sequences of the invention can be used in the preparation of a DNA vaccine to vaccinate fish against PD infection. DNA vaccination refers to the induction of an immune response to one or more antigens that are expressed in vivo from a gene inserted in a DNA plasmid which has been inoculated directly into the vaccinated fish. Thus in a second aspect of the invention there is provided for a DNA vaccine comprising a pharmaceutically acceptable carrier and a DNA plasmid in which a nucleotide sequence encoding one or more PDV structural proteins is operably linked to a transcriptional regulatory sequence.

Preferably the nucleotide sequence to be used in the DNA plasmid is a nucleotide sequence comprising the nucleotide sequence depicted in SEQ ID NO 1 or a nucleotide sequence comprising the nucleotide sequence depicted in SEQ ID NO 14 or fragments of said nucleotide sequences. Preferred fragments of the nucleotide sequence depicted in SEQ ID NO 1 or 14 are nucleotide fragments 1222–5076, 2068–5076, 2068–3594, 1222–2067, 2068–2280, 2281–3594, 3595–3690 3691–5076 of the sequence depicted in SEQ ID NO 1, and combinations thereof such as for example, fragment 1222–2067 with fragment 2281–3594. Also suitable for use in the DNA plasmid are nucleotide sequences that are complementary to the sequence of SEQ ID NO 1 or SEQ ID NO 14 or nucleotide sequences of which the sequence homology with the sequence depicted in SEQ ID NO 1 or SEQ ID NO 14 is at least 70%, preferably 80%, and more preferably 90%. The sequence homology between the nucleotide sequences that are suitable for use in the DNA plasmid is determined as described earlier.

DNA plasmids that are suitable for use in a DNA vaccine according to the invention are conventional cloning or expression plasmids for bacterial, eukaryotic and yeast host cells, many of which are commercially available. Well known examples of such plasmids are pBR322 and pcDNA3 (Invitrogen). The DNA plasmids according to the invention should be able to induce protein expression of the nucleotide sequences. The DNA plasmid can comprise one or more nucleotide sequences according to the invention. In addition, the DNA plasmid can comprise other nucleotide sequences such as the immune-stimulating oligonucleotides having unmethylated CpG dinucleotides, or nucleotide sequences that code for other antigenic proteins or adjuvating cytokines.

Transcriptional regulatory sequences that are suitable for use in a DNA plasmid according to the invention comprise promoters such as the (human) cytomegalovirus immediate early promoter (Seed, B. et al., Nature 329, 840–842, 1987; Fynan, E. F. et al., PNAS 90, 11478–11482,1993; Ulmer, J. B. et al., Science 259, 1745–1748, 1993), Rous sarcoma virus LTR (RSV, Gorman, C. M. et al., PNAS 79, 6777–6781, 1982; Fynan et al., supra; Ulmer et al., supra), the MPSV LTR (Stacey et al., J. Virology 50, 725–732, 1984), SV40 immediate early promoter (Sprague J. et al., J. Virology 45, 773,1983), the metallothionein promoter (Brinster, R. L. et al., Nature 296, 39–42, 1982), the major late promoter of Ad2, the β-actin promoter (Tang et al., Nature 356, 152–154, 1992). The regulatory sequences may also include terminator and polyadenylation sequences. Amongst the sequences that can be used are the well known bovine growth hormone polyadenylation sequence, the SV40 polyadenylation sequence, the human cytomegalovirus (hCMV) terminator and polyadenylation sequences.

The DNA plasmid comprising a nucleotide sequence according to the present invention operably linked to a transcriptional regulatory sequence for use in the vaccine according to the invention can be naked or can be packaged in a delivery system. Suitable delivery systems are lipid vesicles, Iscoms, dendromers, niosomes, polysaccharide matrices, and the like. Also very suitable as delivery system are attenuated live bacteria such as Salmonella.

The nucleotide sequences according to the invention can additionally be used in the production of a vector vaccine to vaccinate fish against PD. A vector vaccine is understood to be a vaccine in which a live, attenuated bacteria or virus has been modified so that it contains one or more heterologous nucleotide sequences inserted into its genetic material. These so called vector bacteria or viruses are capable of coexpressing the heterologous proteins encoded by the inserted nucleotides. Thus in a third aspect the invention provides for a vector vaccine comprising a live attenuated bacteria or virus which have been modified to comprise in their genetic material one or more of the nucleotide sequences of the present invention. Very suitable for use as a vaccine vector are, for example, vaccinia virus or Semliki forest virus The nucleotide sequences according to the invention can also be used for the recombinant production of structural PD proteins, substantially free from other PD proteins. Thus in a fourth aspect the invention provides for the structural proteins from PD virus. More specifically the invention provides for a PD capsid protein, the PD envelope proteins E1, E2, and E3, and the 6K protein. In particular, there is provided for a capsid protein having the amino acid sequence depicted in SEQ ID NO 4 or a derivative thereof, an E3 protein having the amino acid sequence depicted in SEQ ID NO 5 or a derivative thereof, an E2 protein having the amino acid sequence depicted in SEQ ID NO 6 or a derivative thereof, an E1 protein having the amino acid sequence depicted in SEQ ID NO 8 or a derivative thereof, and a 6K protein having the amino acid sequence depicted in SEQ ID NO 7, SEQ ID NO 15 or a derivative thereof.

Derivative proteins are understood to be proteins which have alterations in the amino acid sequencers) of the present invention which do not affect the antigenic and/or immunogenic characteristics of these proteins, that is, these derivative proteins are still capable of inducing the production of antibodies that recognise and (cross)react with the PD virus and/or inducing an immune response in fish that protects against PD infection. Antigenic characteristics are understood to be the ability to induce production of antibodies that recognise and (cross)-react with the PD virus. Immunogenic characteristics are understood to be the ability to induce an immune response in fish that protects against infection with PD. The alterations that can occur in a sequence according to the present invention could, for instance, result from conservative amino acid substitutions, deletions, insertions, inversions or additions of (an) amino acid(s) in the overall sequence. Amino acid substitutions that are expected not to alter the immunological properties have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information, Lipman and Pearson developed a method for rapid and sensitive protein comparison (Science, 1985, vol. 227, 1435–1441) and determining the functional similarity between proteins and peptides having sequence homology. The derivative proteins according to the invention are still capable to induce the production of antibodies that recognise and (cross)-react with the PD virus and/or to induce an immune response in the fish that protects against PD infection. The capsid, E1, E2, E3, and 6K proteins derived from Sleeping Disease (SD) virus are such derivative proteins according to the invention. These proteins have an amino acid sequence that is identical or almost identical to those of the PD virus as depicted in SEQ ID NO 4 to 8 or 15. These proteins are capable to raise antibodies that recognize and cross-react with PD virus as well as SD virus. Other derivatives are protein fragments that are still capable to induce the production of antibodies that recognise and (cross)-react with the PD virus and/or to induce an immune response in the fish.

The proteins according to the invention can be prepared via standard recombinant protein expression techniques. For this purpose a nucleotide sequence encoding one or more of the proteins according to the invention or a multimere of said protein is inserted into an expression vector. Preferably the nucleotide sequence is a nucleotide sequence comprising the nucleotide sequence depicted in SEQ ID NO 1 or SEQ ID NO 14 or one or more fragments of these sequences. Preferred fragments of the nucleotide sequences according to the invention are nucleotide fragments 1222–5076, 2068–5076, 2068–3594, 1222–2067, 2068–2280, 2281–3594, 3595–3690 3691–5076 of the sequence depicted in SEQ ID NO 1, and combinations thereof such, for example, fragment 1222–2067 with fragment 2281–3594. Further preferred fragments according to the invention are fragments of the nucleotide sequence depicted in SEQ ID NO 15 such as for example the nucleotide sequence depicted by nucleotides 3595–3690 of SEQ ID NO 1. Also suitable are nucleotide sequences that are complementary to the sequence of SEQ ID NO 1 or SEQ ID NO 14 or nucleotide sequences of which the sequence homology with the sequence depicted in SEQ ID NO 1 or SEQ ID NO 14 is at least 70%, preferably 80%, and more preferably 90%. The sequence homology between the nucleotide sequences that are suitable for use in the DNA plasmid is determined as described earlier.

Suitable expression vectors are, amongst others, plasmids, cosmids, viruses and YAC's (Yeast Artificial Chromosomes) which comprise the necessary control regions for replication and expression. The expression vector can be brought to expression in a host cell. Suitable host cells are, for instance, bacteria, yeast cells and mammalian cells. Such expression techniques are well known in the art (Sambrooke et al., Molecular Cloning: a Laboratory Manual, Cold Spring Harbor Laboratory Press, Cold Spring Harbor, 1989). The expressed proteins can be isolated and purified from the medium. Expression of the whole p130 ORF (nucleotide fragment 997 to 5076 of SEQ ID NO 1) might lead to the forming of virus-like particles due to the spontaneous assemblance of the structural proteins.

The invention furthermore provides for a vaccine comprising one or more of the structural PD proteins and a pharmaceutically acceptable carrier. More specifically, a vaccine according to the invention comprises a capsid protein having an amino acid sequence depicted in SEQ ID NO 4 or a derivative thereof, an E3 protein having an amino acid sequence depicted in SEQ ID NO 5 or a derivative thereof, an E2 protein having an amino acid sequence depicted in SEQ ID NO 6 or a derivative thereof, an E1 protein having an amino acid sequence depicted in SEQ ID NO 8 or a derivative thereof, a 6K protein having an amino acid sequence depicted in SEQ ID NO 7 or SEQ ID NO 15 or a derivative thereof, or a mixture comprising two or more of the proteins according to the invention. Preferably the vaccine according to the invention comprises the E2 protein, and optionally the capsid protein. Also preferred is a vaccine comprising all structural proteins of PD; these proteins can spontaneously form virus-like particles, thus providing a vaccine that closely resembles that of the whole pathogen. Vaccines according to the invention are suitable for use as a marker vaccine to distinguish between vaccination and infection by PD in the field. A preferred vaccine according to the invention is a marker vaccine comprising a 6K protein having the amino acid sequence depicted in SEQ ID NO 7.

A vaccine according to the invention can be prepared according to techniques well known to the skilled practitioner. General techniques for the preparation of DNA vaccines have been widely described, for example in EP patent 0 773 295 and U.S. Pat. No. 5,580,859.

Vaccines according to the invention comprise an effective amount of the afore-mentioned DNA plasmids, vector bacteria or virus, or proteins and a pharmaceutically acceptable carrier. The term "effective" as used herein is defined as the amount sufficient to induce an immune response in the target fish. The amount of plasmid, vector or protein will depend on the type of plasmid or vector, the route of administration, the time of administration, the species of the fish as well as age, general health and diet.

In general, a dosage of 0.01 to 1000 µg protein per kg body weight, preferably 0.5 to 500, and more preferably 0.1 to 100 µg protein can be used. With respect to the DNA vaccines, generally a minimum dosage of 10 pg. up to dosages of 1000 µg of plasmid have been described to be sufficient for a suitable expression of the antigens in vivo.

Pharmaceutically acceptable carriers that are suitable for use in a vaccine according to the invention are sterile water, saline, aqueous buffers such as PBS and the like. In addition, a vaccine according to the invention may comprise other additives such as adjuvants, stabilisers, anti-oxidants and others.

Suitable adjuvants include, amongst others, aluminium hydroxide, aluminium phosphate, amphigen, tocophenols, monophosphenyl lipid A, muramyl dipeptide, oil emulsions, glucans, carbomers, block-copolymers, cytokines and saponins such as Quil A. The amount of adjuvant added depends on the nature of the adjuvant itself.

Suitable stabilisers for use in a vaccine according to the invention are, for example, carbohydrates including sorbitol, mannitol, starch, sucrose, dextrin, and glucose, proteins such as albumin or casein, and buffers like alkaline phosphates.

The vaccines according to the invention are administered to the fish via injection, spray, immersion or peroral. The administration protocol can be optimised in accordance with standard vaccination practice.

The nucleotide sequences and the proteins according to the invention are also suitable for use in diagnostics. The nucleotide sequences or fragments thereof can be used to detect the presence of PD virus in the fish. A primer spanning the C-terminal part of E2/6K/N-terminal part of E1 (see FIG. 2) was used in RT-PCR to succesfully detect the presence of PD virus in a clinical specimen of a PD outbreak. The proteins can be used to detect the presence of antibodies in the fish.

The proteins according to the invention can additionally be used for the production of antibodies, using the general techniques available to the practitioner in the field. Preferably the proteins are used to produce specific monoclonal antibodies. The obtained antibodies may be utilised in diagnostics, to detect PD virus in the field, or in the fish.

Thus, in another aspect, the present invention provides for a diagnostic kit comprising one or more nucleotide sequences according to the invention, or one or more structural proteins according to the invention, or antibodies obtained with said proteins. Antibodies according to the invention can be prepared according to standard techniques. Procedures for immunising animals, e.g. mice with proteins and selection of hybridomas producing immunogen specific monoclonal antibodies are well known in the art (see for example Coligan et al. (eds), Current protocols in Immunology, 1992; Kohler and Milstein, *Nature* 256:495–497, 1975; Steenbakkers et al., Mol. Biol. Rep. 19:125–134, 1994).

The following examples are to illustrate the invention and should not be interpreted to limit the invention in any way.

FIG. 1: structural organisation of the various cloned nucleotide sequences coding for the PD structural proteins.

FIG. 2: Nucleotide sequence of C-terminus of E2 gene/ "long" 6K gene/N-terminus of E1 gene. The putative cleavage sites between the E2/6K protein and 6K/E1 protein are presented by the vertical line (|)The nucleotide sequence encoding the "long" 6K protein is 204 nucleotides long and encodes a protein of 68 amino acids. The numbering between brackets on the right of the sequence refers to the nucleotide-and amino acid residues of the 6K gene or protein respectively. At nucleotide position 44 of the nucleotide sequence encoding the 6K gene the G-residue can be replaced with an A residue, resulting in a 6K protein with an N residue at amino acid position 15 of the amino acid sequence depicted in the figure.

EXAMPLES

Cells and Virus

Isolation and cultivation of a salmon PD virus (SPDV) strain was carried out in general as described in EP-A-712926. The F93125 isolate of SPDV was grown in Chinook salmon embryo (CHSE-214) cells as previously described (R. T. Nelson et al. (1995) Isolation of toga-like virus from farmed Atlantic salmon Salmo salar with pancreas disease. Diseases of Aquatic Organisms 22, pp. 25–32). For virus purification purposes, monolayer cultures of CHSE-214 grown to ~80% confluence in 75 cm$^2$ flasks were infected with 1 ml virus to give a multiplicity of infection of ~1. After 1 hr adsorption an additional 14 ml supplemented Eagle's minimal essential medium (MEM) was introduced to each flask. The virus infected flasks were incubated at 15° C. for 7 or 8 days, when virus-induced cytopathic effect was evident, and the supernatant was collected.

Virus Purification

The supernatant (typically 500 ml from virus-infected cells was clarified at 3000 g for 20 min. Polyethyleneglycol (PEG) and NaCl were added to give final concentrations of 6% and 2.2% respectively. Following overnight incubation at 4° C. the PEG precipitate was collected by centrifugation for 2 h at 3000 g. The resultant pellet was resuspended in PBS (1–2 ml) and, after clarification at 1000 g for 5 minutes, the crude virus suspension was fractionated by equilibrium density centrifugation using 11 ml gradients (20–60% w/w in PBS) of sucrose. After centrifugation for 18 hr at 75000 g at 4° C., 1 ml fractions were collected from the bottom of the gradient. Fractions containing virus were identified by immunoblotting using an PD-specific mouse monoclonal antibody (Welsh et al., submitted 1999).

Production of PD Virus cDNA Clones

Viral RNA was extracted from gradient-purified PD virus and virus-infected cells using RNA isolator (Genosys) and stored as ethanol precipitates. A cDNA library was made by random priming with RNA extracted from gradient-purified virus. This library consisted of clones containing inserts (250–500 bp) in the vector pUC18 (Sureclone ligation Kit, Pharmacia). Clones were selected randomly from the library and following sequencing and analysis using the BLAST program (University of Wisconsin, Genetics Computer Group) were mapped to the alphavirus genome. The sequences of three clones, N11, N38 and N50, were used to design oligonucleotide primers that were used in reverse transcription-polymerase chain reaction (RT-PCR) to amplify 3 overlapping fragments encompassing the 5.2 kb region at the 3'terminus of the PD genome. The incorporation of Not I sites into the primers facilitated the restriction ligation of two of these fragments into the Not I site of vector pBluescript (Stratagene). PCR was carried out using Expand Long Template PCR System (Boehringer Mannheim) at 94° C. for 30s 60° C. for 30s, 68° C. for 2 min. Another clone was produced using 3'RACE (M. A. Frohmann et al., 1998; Rapid production of fill-length cDNA's from rare transcripts using a single gene-specific oligonucleotide primer. *Proc. Natl. Acad. Sci.USA*. 85, pp. 8998–9002). The reaction was performed using a 5'/3' RACE kit (Boehringer Mannheim) with some modifications. Thus, RNA from gradient-purified virus was independently subjected to first-strand synthesis and the resultant cDNA's were amplified by PCR at 94° C. for 30s, 60° C. for 30s, 68° C. for I min.

Sequencing of PD Virus cDNA Clones

Cycle sequencing was performed using the ABI PRISM dye terminator ready reaction kit on purified plasmid DNA following the manufacturers protocol (Perkin Elmer Cetus). Electropherograms were interpreted using the Sequence Navigator software (Perkin Elmer Cetus). The complete nucleotide sequence of the 3'terminal 5.2 kb region of the PD virus RNA is presented in SEQ ID NO1.

An RT-PCR and sequence analysis using primers flanking the C-termninus of E2 and the N-terminus of E1 for viral RNA extracted directly from PD infected pancreas tissue revealed a longer 6K-encoding nucleotide sequence than the one depicted by nucleotides 3595–3690 of SEQ ID NO 1. The nucleic acid encoding the full-length 6K protein as well as the deduced amino acid sequence are shown in FIG. 2.

SPDV pFastBac1 and pcDNA3.1(+) Constructs

Using standard cloning techniques (Sambrooke et al., Molecular Cloning: a Laboratory Manual, Cold Spring Harbor Laboratory Press, Cold Spring Harbor, 1989) four clones representing the SPDV structural region have been created in the vector pFastBac1 (Gibco BRL) for expression in the baculovirus system. These clones have also been created in the expression vector pcDNA3.1 (Invitrogen) for monoclonal antibody characterisation and use as a DNA vaccine. Details of how these clones have been produced are as follows:

Clone 1.

p130 encodes the complete structural gene region from the 1st ATG of the capsid protein to the poly(A) tract (3944nt). cDNA was produced from viral RNA by RT-PCR using the following primers:

5' forward primer (5'130Not1): 5'-TGC ATG CGG CCG CAT GTT TCC CAT GCA ATT CAC CAA C-3' (SEQ ID NO 9)

3' inverse primer (3'130Not1) (sequence 5' to 3'): 5'-TGC ATG CGG CCG CTT GTA TTG AAA ATT TTA AAA CCA A-3' (SEQ ID NO 10)

These primers contain a 5 nucleotide stretch (ensures restriction enzyme recognition) followed by a Not1 site then the appropriate SPDV sequence (highlighted in the attached sequence, from 1222 to 1245 for 5'130Not1 and from 5143 to 5166 for 3'130Not1). The 3944nt cDNA product was cloned into the Not1 site in both pFastBac1 and pcDNA3.1.

Clone 2.

p98 encodes for E3, E2, 6K and E1 to the poly(A) tract (3098nt). cDNA was produced from viral RNA by RT-PCR using the following primers:

5' forward primer (5'E3Not1): 5'-TGC ATG CGG CCG CAT GAC ACG CGC TCC. GGC CCT CCT G-3' (SEQ ID NO 11)

3' inverse primer (3'130Not1): 5'-TGC ATG CGG CCG CTT GTA TTG AAA ATT TTA AAA CCA A-3' (SEQ ID NO 10)

The primer 5'E3Not1 contains a 5 nucleotide stretch (ensures restriction enzyme recognition) followed by a Not1 site, an ATG (artificial start codon) then the appropriate SPDV sequence (from 2067 to 2088) The primer 3'130Not1 is as described above in Clone1. The 3098nt cDNA product was cloned into the Not1 site in both pFastBac1 and pcDNA3.1.

Clone 3.

pE2 encoding the E3 and E2 glycoproteins (1527nt). cDNA was produced from viral RNA by RT-PCR using the following primers:

5' forward primer (5'E3Not1): 5'-TGC ATG CGG CCG CAT GAC ACG CGC TCC GGC CCT CCT G-3'(SEQ ID NO 11)

3' inverse primer (3'E2Not1): 5'-TGC ATG CGG CCG CTC ACG CGC GAG CCC CTG GTA TGC AAC A-3' (SEQ ID NO 12)

The primer 5'E3Not1 is as described above in Clone2. The primer 3'E2Not1 contains a 5 nucleotide stretch (ensures restriction enzyme recognition) followed by a Not1 site, a TGA (artificial stop codon) then the appropriate SPDV sequence (highlighted in the attached sequence, from 3571 to 3594). The 1527nt cDNA product was cloned into the Not1 site in both pFastBac1 and pcDNA3.1.

Clone 4.

E2 encoding the E2 glycoprotein (1314nt). cDNA was produced from viral RNA by RT-PCR using the following primers:

5' forward primer (5'E2Not1): 5'-TGC ATG CGG CCG CAT GGC TGT GTC TAC GTCGCCTGC C-3' (SEQ ID NO 13)

3' inverse primer (3'E2Not1): 5'-TGC ATG CGG CCG CTC ACG CGC GAG CCC CTG GTA TGC AAC A-3' (SEQ ID NO 12).

The primer 5'E2Not1 contains a 5 nucleotide stretch (ensures restriction enzyme recognition) followed by a Not1 site, an ATG (artificial start codon) then the appropriate SPDV sequence (from 2281 to 2301). The primer 3'E2Not1 is as described above in Clone 3. The 1314nt cDNA product was cloned into the Not1 site in both pFastBac1 and pcDNA3.1.

Insect cells (SF-9)were infected with the four recombinant baculovirus constructs. Using monoclonals that were raised against whole-inactivated PD virus, an IFT staining was performed on these recombinant baculovirus infected SF-9 cells. All produced proteins reacted positively with the monoclonals, indicating that the recombinant proteins possess the wild-type epitopes.

Challenge Experiments

The proteins produced by all four constructs were collected using Triton extraction. The proteins were BPL inactivated to prevent possible spread of surviving recombinant baculoviruses in the environment. The proteins were formulated into water-in-oil based vaccine formulations and injected in a 0.2 ml vaccine volume.

ELISA analysis using anti-PD-E2 monoclonals (2D9 capture and 7A2) showed that the amount of reactive epitopes per dose recombinant vaccine was comparable or even higher than the amount of epitopes found in a dose of the conventional inactivated PD virus vaccine.

A standardised challenge experiment performed at 8 weeks post-vaccination in Atlantic salmon fish showed that protection against challenge with salmon PD virus could be obtained with these recombinant sub-unit vaccines. In the experiment, lesions in pancreas, skeletal muscle and heart muscle were scored in the ordinary way. Significant levels were calculated from Kruskal-Wallis one-way analysis of variance (non-parametric test). The vaccine formulation comprising the E2 or E2-E3 proteins gave similar levels of protection as obtained by the inactivated PD virus vaccine, while vaccines containing the recombinant proteins resulting from the p130 and p98 constructs, respectively, were less protective then the PD virus vaccine.

Production of Antibodies.

DNA vaccination with proteins obtained from expression of the p130 nucleotide construct was carried out in mice to test for the antigenic properties of the recombinant proteins. After two intramuscular inoculations with p130-pcDNA3.1 recombinant expression plasmids (see clone 1), the sera of mice showed an antibody reaction with in vitro produced PD virus.

What is claimed is:

1. An isolated structural protein of Fish Pancreatic Disease virus, wherein the protein is a capsid protein, wherein the protein comprises an amino acid sequence comprising SEQ ID NO:4.

2. A pharmaceutical composition, comprising:

the isolated protein of claim 1 and a pharmaceutically acceptable carrier.

3. A vaccine, comprising:

the isolated structural protein of claim 1 and a pharmaceutically acceptable carrier.

4. A diagnostic kit, comprising:

the isolated protein of claim 1.

* * * * *